United States Patent [19]
Greenwald et al.

[11] Patent Number: 6,113,906
[45] Date of Patent: *Sep. 5, 2000

[54] WATER-SOLUBLE NON-ANTIGENIC POLYMER LINKABLE TO BIOLOGICALLY ACTIVE MATERIAL

[75] Inventors: Richard B. Greenwald, Somerset; Anthony J. Martinez, Hamilton Square, both of N.J.

[73] Assignee: Enzon, Inc., Piscataway, N.J.

[ * ] Notice: This patent is subject to a terminal disclaimer.

[21] Appl. No.: 09/222,463

[22] Filed: Dec. 29, 1998

Related U.S. Application Data

[63] Continuation of application No. 08/821,055, Mar. 20, 1997, Pat. No. 5,919,455, and a continuation-in-part of application No. 08/143,403, Oct. 27, 1993, Pat. No. 5,643,575, and a continuation-in-part of application No. 08/696,198, Aug. 13, 1996, Pat. No. 5,681,567.

[51] Int. Cl.[7] .................. A61K 39/395; A61K 39/44; C08G 65/331; C08G 65/332; C08G 65/333

[52] U.S. Cl. ..................... 424/194.1; 424/178.1; 525/54.1; 525/54.11; 525/403; 525/408; 530/391.1; 530/395; 530/403; 530/405; 530/408

[58] Field of Search ............... 424/178.1, 179.1; 525/54.1, 403, 408; 530/406, 410; 560/182; 514/449; 549/510, 433

[56] References Cited

U.S. PATENT DOCUMENTS

| | | | |
|---|---|---|---|
| 4,101,380 | 7/1978 | Rubinstein et al. | 195/63 |
| 4,179,337 | 12/1979 | Davis et al. | 435/181 |
| 4,275,000 | 6/1981 | Ross . | |
| 4,680,338 | 7/1987 | Sundoro . | |
| 4,766,106 | 8/1988 | Katre et al. | 514/12 |
| 4,846,548 | 7/1989 | Klainer | 350/96.29 |
| 4,889,916 | 12/1989 | Packard et al. | 575/54.1 |
| 4,904,582 | 2/1990 | Tullis . | |
| 5,091,176 | 2/1992 | Braatz et al. . | |
| 5,091,542 | 2/1992 | Ahlem et al. | 548/521 |
| 5,093,531 | 3/1992 | Sano et al. . | |
| 5,122,614 | 6/1992 | Zalipsky | 548/520 |
| 5,183,660 | 2/1993 | Ikeda et al. | 424/94.3 |
| 5,214,131 | 5/1993 | Sano et al. . | |
| 5,219,564 | 6/1993 | Zalipsky et al. | 424/78.17 |
| 5,229,490 | 7/1993 | Tam | 530/324 |
| 5,252,714 | 10/1993 | Harris et al. . | |
| 5,281,698 | 1/1994 | Nitecki | 530/351 |
| 5,298,643 | 3/1994 | Greenwald | 558/606 |
| 5,321,095 | 6/1994 | Greenwald | 525/404 |
| 5,349,001 | 9/1994 | Greenwald et al. | 525/408 |
| 5,382,657 | 1/1995 | Karasiewicz et al. | 530/351 |
| 5,514,379 | 5/1996 | Weissieder et al. | 424/426 |
| 5,543,158 | 8/1996 | Gref et al. | 424/501 |
| 5,643,575 | 7/1997 | Martinez et al. | 424/194.1 |
| 5,681,567 | 10/1997 | Martinez et al. | 424/178.1 |
| 5,919,455 | 7/1999 | Greenwald et al. | 424/178.1 |
| 5,932,462 | 8/1999 | Harris et al. | 435/188 |

FOREIGN PATENT DOCUMENTS

| | | |
|---|---|---|
| 0236987 | 9/1987 | European Pat. Off. . |
| 0510356 | 10/1992 | European Pat. Off. . |
| 0539167 | 4/1993 | European Pat. Off. . |
| 0 809 996 A2 | 3/1997 | European Pat. Off. . |
| 9102763 | 3/1991 | WIPO . |
| 9324476 | 12/1993 | WIPO . |
| WO 95/09883 | 4/1995 | WIPO . |

OTHER PUBLICATIONS

Wie et al (1981) Int. Arch. Allergy Appl. Immun. 64:84–99.

Savoca et al (1979) Biochim. Biophys. Acta 578:47–53.

Sehron (1991) Int. Arch. Allergy Appl. Immunol. 94:11–20.

Nucci et al (1991) Advanced Drug Delivery Reviews 6:133–151.

Kanuf et al., "Relationship of Effective Molecular Size:," J Biol Chen. 263:15064–70 (1994).

Nathan et al, "Polyethylene Gylcol–Lysine Copolymers:," Polymers Pelprnts 31:213–214(1992).

Monfardini, C., et al., A Branched Monomethoxypoly (ethylene glycol) for Protein Modification, bioconjugate Chemistry, vol. 6, No. 1, pp. 62–69 (1995).

Yamasaki, N., et al., Novel Polyethylene Glycol Derivatives for Modification of Proteins, Agric. Biol. Chem. 52(8), pp. 2125–2127 (1988).

Yamasaki, N. et al., "Some Properties of Ricin D Modified with a Methoxypolyethylene Glycol Derivative" Agric. Biol. Chem., 54(10) 2635–2640, (1990).

Kodera, Y. et al. "Chemical Modification of L–Asparaginase With a Comb–Shaped–Copolymer of Polyethylene Glycol Derivative and Maleic Anhydride", Biochemical and Biophysical Research Communications, vol. 184, No. 1, 1992Apr. 15, 1992, pp. 144–148.

Bogdanov, A. et al. "A New Marcomolecul as a Contrast Agent for MR Angiography: Preparation, Properties, and Animal Studies" Radiology 187: 701–706 (1993) Mailed May 20, 1993.

Nishimura et al, Enzyme 26, pp. 49–53 (1981).

Kimura et al, Proceeding of the Society for Experimental Biology and Medicine, 188, pp. 364–369 (1988).

Zalipsky et al, Eur. Polym. J., vol. 19, No. 12, pp. 1177–1183, (1983).

Ouchi et al, Drug Design and Discovery, vol. 9, pp. 93–105 (1992).

(List continued on next page.)

*Primary Examiner*—Robert E. Sellers
*Attorney, Agent, or Firm*—Roberts & Mercanti, LLP

[57] ABSTRACT

Branched, substantially non-antigenic polymers are disclosed. Conjugates prepared with the polymers and biologically active molecules such as proteins and peptides demonstrate extended circulating life in vivo. Substantially fewer sites on the biologically active material are used as attachment sites. Methods of forming the polymer, conjugating the polymers with biologically active moieties and methods of using the conjugates are also disclosed.

20 Claims, No Drawings

OTHER PUBLICATIONS

The Journal of Biological Chemistry vol. 263, No. 29, Issue of Oct. 15, pp. 15064, 15070 (1988).
Eur. Polym. J. vol. 19, No. 12, pp. 1177–1183 (1983).
Biotechnology and Applied Biochemistry 9. 258–268 (1987).
Journal of Controlled Release 10 (1989) 145–154 (1989).

Advanced Drug Delivery Reviews 6 (1991) 133–151.
Cancer Biochem. Biophys. (1984) vol. 7 pp. 175–186.
Polmer Bulletin 18. 487–493 (1987).
Journal of Polymer Science: Polymer Chemistry Edition. vol. 22 pp. 341–352 (1984).
Int. Arch Allergy Appl. Immun. 64:84–99 (1981).

WATER-SOLUBLE NON-ANTIGENIC POLYMER LINKABLE TO BIOLOGICALLY ACTIVE MATERIAL

CROSS REFERENCE TO RELATED APPICATIONS

This application is a continuation of U.S. patent application Ser. No. 08/821,055 filed Mar. 20, 1997, now U.S. Pat. No. 5,919,455, which is a continuation-in-part of U.S. patent application Ser. No. 08/143,403, filed Oct. 27, 1993, now U.S. Pat. No. 5,643,575, and Ser. No. 08/696,198 filed Aug. 13, 1996, now U.S. Pat. No. 5,681,567, the contents of which are incorporated herein by reference.

BACKGROUND OF THE INVENTION

Field of the Invention

The present invention relates to branched polymers which are useful in extending the in vivo circulating life of biologically active materials. The invention also relates to conjugates made with the polymers.

Some of the initial concepts of coupling peptides or polypeptides to poly(ethylene glycol) PEG and similar water-soluble poly(alkylene oxides) are disclosed in U.S. Pat. No. 4,179,337, the disclosure of which is incorporated herein by reference. Polypeptides modified with these polymers exhibit reduced immunogenicity/antigenicity and circulate in the bloodstream longer than unmodified versions.

To conjugate poly(alkylene oxides), one of the hydroxyl end-groups is converted into a reactive functional group. This process is frequently referred to as "activation" and the product is called an "activated poly(alkylene oxide)". Other substantially non-antigenic polymers are similarly "activated" or functionalized.

The activated polymers are reacted with a therapeutic agent having nucleophilic functional groups that serve as attachment sites. One nucleophilic functional group commonly used as an attachment site is the ε-amino groups of lysines. Free carboxylic acid groups, suitably activated carbonyl groups, oxidized carbohydrate moieties and mercapto groups have also been used as attachment sites.

Insulin and hemoglobin were among the first therapeutic agents conjugated. These relatively large polypeptides contain several free ε-amino attachment sites. A sufficient number of polymers could be attached to reduce immunogenicity and increase the circulating life without significant loss of biologic activity.

Excessive polymer conjugation and/or conjugation involving a therapeutic moiety's active site where groups associated with bioactivity are found, however, often result in loss of activity and thus therapeutic usefulness. This is often the case with lower molecular weight peptides which have few attachment sites not associated with bioactivity. Many non-peptide therapeutics also lack a sufficient number of attachment sites to obtain the benefit of polymer modification.

One suggestion for overcoming the problems discussed above is to use longer, higher molecular weight polymers. These materials, however, are difficult to prepare and expensive to use. Further, they provide little improvement over more readily available polymers.

Another alternative suggested is to attach two strands of polymer via a triazine ring to amino groups of a protein. See, for example, *Enzyme*, 26, 49–53 (1981) and *Proc. Soc. Exper. Biol. Med.*, 188, 364–9 (1988). Triazine, however, is a toxic substance which is difficult to reduce to acceptable levels after conjugation. In addition, triazine is a planar group and can only be double-polymer substituted. The planar structure rigidly locks the two polymer chains in place. This limits the benefits of polymer conjugation to about the same as that obtained by increasing polymer chain length. Thus, non-triazine-based activated polymers would offer substantial benefits to the art.

In the above-mentioned cases, however, the biologically active polymer conjugates were formed having substantially hydrolysis-resistant bonds (linkages) between the polymer and the parent biologically-active moiety. Thus, long-lasting conjugates which are of a rather permanent nature rather than prodrugs per se (where the parent molecule is eventually liberated in vivo were prepared.

In addition, over the years, several methods of preparing prodrugs have also been suggested. Prodrugs include chemical derivatives of a biologically-active parent compound which, upon administration, will eventually liberate the active parent compound in vivo. Use of prodrugs allows the artisan to modify the onset and/or duration of action of a biologically-active compound in vivo. Prodrugs are often biologically inert or substantially inactive forms of the parent or active compound. The rate of release of the active drug is influenced by several factors including the rate of hydrolysis of the linker which joins the parent biologically active compound to the prodrug carrier.

Prodrugs based on ester or phosphate linkages have been reported. In most cases, the particular type of ester linkage used to form the prodrug provides $T_{1/2}$ for hydrolysis of up to several days in aqueous environments. Although one would expect a prodrug to have been formed, most of the conjugate is eliminated prior to sufficient hydrolysis being achieved in vivo. It would therefore be preferable to provide prodrugs which have a linkage which allows more rapid hydrolysis of the polymer-drug linkage in vivo so as to generate the parent drug compound more rapidly.

It has also been surprisingly found that when only one or two polymers of less than 10,000 molecular weight (each) are conjugated to biologically-active compounds such as organic moieties, the resulting conjugates are often rapidly eliminated in vivo. In fact, such conjugates are often so rapidly cleared from the body that even if a substantially hydrolysis-prone ester linkage is used, not enough of the parent molecule is regenerated.

Even though previous prodrugs based on conjugates of a parent drug compound on a water soluble polymer have not been successful for a variety of reasons, including excessively slow hydrolysis of the linkage, work in this area has continued. There is still a need in improvements in polymer-based prodrugs and, in particular, ways of significantly increasing the payload of the polymer portion of the prodrug. The present invention addresses these shortcomings.

SUMMARY OF THE INVENTION

In one aspect of the invention, there are provided branched, substantially non-antigenic polymers corresponding to the formula:

$$(R)_n\text{L-A} \qquad (I)$$

wherein (R) includes a water-soluble non-antigenic polymer;

(n)=2 or 3;

(L) is an aliphatic linking moiety covalently linked to each (R); and (A) represents an activating functional group capable of undergoing nucleophilic substitution.

For example, (A) can be a group which is capable of bonding with biologically active nucleophiles or moieties capable of doing the same. In particularly preferred aspects of the invention, (R) includes a poly(alkylene oxide) PAO such as a poly(ethylene glycol) (hereinafter: PEG).

One preferred embodiment of the invention provides branched polymers containing a terminal carboxylic acid group which is useful in the formation of ester-based prodrugs. The branched polymers are of the formula:

$$(R)_n L\text{—COOH} \qquad (Ia)$$

where (R), (n), and (L) are as defined above.

Another preferred embodiment of the invention includes branched polymers of the same formula set forth above, i.e.: $(R)_n L\text{-A}$, except that (L) is selected form the group consisting of

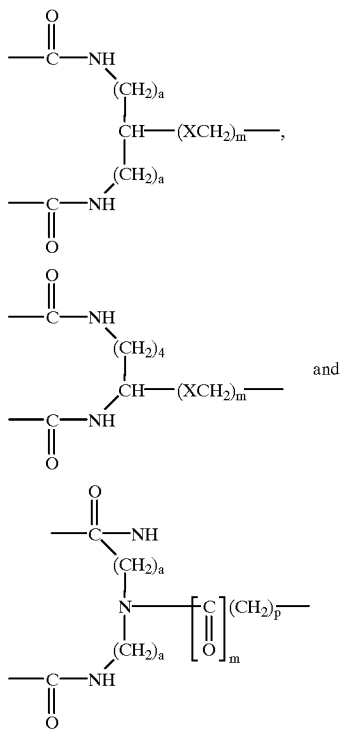

where (a) is an integer of from about 1 to about 5;
X is O, NQ, S, SO or $SO_2$; where Q is H, $C_{1-8}$ alkyl, $C_{1-8}$ branched alkyl, $C_{1-8}$ substituted alkyl, aryl or aralkyl;
(m) is 0 or 1;
(p) is a positive integer, preferably from about 1 to about 6;
(R) is as defined above and (n) is 2; and
(A) is as defined above, including COOH as set forth in Formula (Ia).

These umbrella-like branched polymers of the present invention (U-PAO's or U-PEG's) react with biologically active nucleophiles to form conjugates. The point of polymer attachment depends upon the functional group (A). For example, (A) can be a succinimidyl succinate or carbonate and react with epsilon amino lysines. Alternatively, (A) can be a carboxylic acid which is capable of reacting with hydroxyl groups found on biologically-active nucleophiles to form ester-linked prodrugs. The branched polymers can also be activated to link with any primary or secondary amino group, mercapto group, carboxylic acid group, reactive carbonyl group or the like found on biologically-active materials. Other groups are apparent to those of ordinary skill in the art.

Other aspects of the invention include conjugates containing biologically-active materials and one or more of the branched polymers described above as well as methods of their preparation. The biologically active materials include proteins, peptides, enzymes, medicinal chemicals or organic moieties whether synthesized or isolated from nature. The methods include contacting a biologically active material containing a nucleophile capable of undergoing a substitution reaction with a branched polymer described above under conditions sufficient to effect attachment while maintaining at least a portion of the biological activity.

The present invention also includes methods of treating various maladies and conditions. In this aspect, a mammal in need of treatment is administered an effective amount of a conjugate containing a biologically-active material such as a protein, enzyme or organic moiety and a branched polymer of the present invention.

One of the chief advantages of the present invention is that the branching of the polymers imparts an umbrella-like three-dimensional protective covering to the materials they are conjugated with. This contrasts with the string-like structure of conventional polymer conjugates. Moreover, the branching of the polymer chains from a common root allows dynamic, non-planar action in vivo. Thus, the branched polymers offer substantial benefits over straight-chained polymers of equivalent molecular weight.

A second advantage of the branched polymers is that they provide the benefits associated with attaching several strands of polymers to a bioeffecting material but require substantially fewer conjugation sites. The advantages of the branched polymers are particularly dramatic for therapeutic agents having few available attachment sites. All the desired properties of polymer conjugation are realized and loss of bioactivity is minimized.

DETAILED DESCRIPTION OF THE INVENTION

1. Polymer Substituents and Formula (I) Defined

The activated branched polymers of the present invention are preferably prepared from poly(alkylene oxides) (PAO's) that are water soluble at room temperatures. Within this group are alpha-substituted polyalkylene oxide derivatives such as methoxypoly (ethylene glycols) (mPEG) or other suitable alkyl substituted PAO derivatives such as those containing mono or bis terminal $C_1$–$C_4$ groups. Straight-chained non-antigenic polymers such as monomethyl PEG homopolymers including

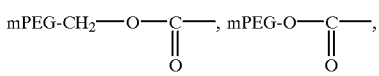

and mPEG—O—$CH_2$—$CH_2$— are preferred. Alternative polyalkylene oxides such as other poly(ethylene glycol) homopolymers, other alkyl-poly(ethylene oxide) block copolymers, and copolymers of block copolymers of poly(alkylene oxides) are also useful.

The polymers of the present invention are represented by Formula (I):

$$(R)_n L\text{-A} \qquad (I)$$

wherein:
(R) includes a water-soluble, substantially non-antigenic polymer;
(n)=2 or 3;
(L) is an aliphatic linking moiety covalently linked to each (R); and (A) represents an activating functional group capable of undergoing nucleophilic substitution.

Each (R) can be a water-soluble, substantially non-antigenic polymer chain. When the polymer chains are PEG or MPEG, it is preferred that each chain have a molecular weight of between about 200 and about 80,000 daltons and preferably between about 2,000 and about 42,000 daltons. Molecular weights of about 5,000 to about 20,000 daltons are most preferred.

Alternative polymeric substances include materials such as dextrans, polyvinyl pyrrolidones, polyacrylamides or other similar non-immunogenic polymers. Such polymers are also capable of being functionalized or activated for inclusion in the invention. The foregoing is merely illustrative and not intended to restrict the type of non-antigenic polymers suitable for use herein.

In another embodiment of the invention, (R) is a branched polymer for secondary and tertiary branching from a bioactive material. Bifunctional and hetero-bifunctional active polymer esters can also be used. The polymers of the present invention can also be copolymerized with bifunctional materials such as poly(alkylene glycol) diamines to form interpenetrating polymer networks suitable for use in permeable contact lenses, wound dressings, drug delivery devices and the like. The stearic limitations and water solubility of such branching will be readily recognized by one of ordinary skill in the art. Preferably, however, the molecular weight of multiple branched polymers should not exceed 80,000 daltons.

As shown in Formula I, 2 or 3 polymer chains, designated (R) herein, are joined to the aliphatic linking moiety (L). Suitable aliphatics include substituted alkyl diamines and triamines, lysine esters and malonic ester derivatives. The linking moieties are preferably non-planar, so that the polymer chains are not rigidly fixed. The linking moiety (L) is also the means for attaching the multiple polymer chains or "branches" to (A), the moiety through which the polymer attaches to bio-effecting materials.

(L) preferably includes a multiple-functionalized alkyl group containing up to 18, and more preferably, between 1–10 carbon atoms. A heteroatom such as nitrogen, oxygen or sulfur may be included within the alkyl chain. The alkyl chain may also be branched at a carbon or nitrogen atom. In another aspect of the invention, (L) is a single nitrogen atom.

(L) and each (R) are preferably joined by a reaction between nucleophilic functional groups on both (R) and (L). Each (R) is suitably functionalized to undergo nucleophilic substitution and bond with (L). Such functionalization of polymers is readily apparent to those of ordinary skill in the art.

A wide variety of linkages are contemplated between (R) and (L). Urethane (carbamate) linkages are preferred. The bond can be formed, for example, by reacting an amino group such as 1,3-diamino-2-propanol with methoxypolyethylene glycol succinimidyl carbonate described in U.S. Pat. No. 5,122,614, the disclosure of which is incorporated herein by reference. Amide linkages, which can be formed by reacting an amino-terminated non-antigenic polymer such as methoxy-polyethylene glycol-amine (mPEG amine) with an acyl chloride functional group.

Examples of other linkages between (R) and (L) include ether, amine, urea, and thio and thiol analogs thereof, as well as the thio and thiol analogs of the above-discussed urethane and amide linkages. The linkages are formed by methods well understood by those of ordinary skill in the art. Other suitable linkages and their formation can be determined by reference to the above-cited U.S. Pat. No. 4,179,337.

The moiety (A) of Formula I represents groups that "activate" the branched polymers of the present invention for conjugation with biologically active materials.

(A) can be a moiety selected from:

I. Functional groups capable of reacting with an amino group such as:
  a) carbonates such as the p-nitrophenyl, or succinimidyl;
  b) carbonyl imidazole;
  c) azlactones;
  d) cyclic imide thiones; or
  e) isocyanates or isothiocyanates.

II. Functional groups capable of reacting with carboxylic acid groups and reactive carbonyl groups such as:
  a) primary amines; or
  b) hydrazine and hydrazide functional groups such as the acyl hydrazides, carbazates, semicarbamates, thiocarbazates, etc.

III. Functional groups capable of reacting with mercapto or sulfhydryl groups such as phenyl glyoxals; see, for example, U.S. Pat. No. 5,093,531, the disclosure of which is hereby incorporated by reference.

IV. Functional groups capable of reacting with hydroxyl groups such as (carboxylic) acids, such as in Formula (Ia) or other nucleophiles capable of reacting with an electrophilic center. A non-limiting list includes, for example, hydroxyl, amino, carboxyl, thiol groups, active methylene and the like.

The moiety (A) can also include a spacer moiety located proximal to the aliphatic linking moiety, (L). The spacer moiety may be a heteroalkyl, alkoxy, alkyl containing up to 18 carbon atoms or even an additional polymer chain. The spacer moieties can added using standard synthesis techniques. It is to be understood that those moieties selected for (A) can also react with other moieties besides biologically active nucleophiles.

One preferred embodiment of the invention provides branched polymers containing a terminal carboxylic acid group which is useful in the formation of ester-based prodrugs. The branched polymers are of the formula:

$$(R)_n L—COOH \tag{Ia}$$

where (R), (n), and (L) are as defined above.

Some particularly preferred compounds within this aspect of the invention include:

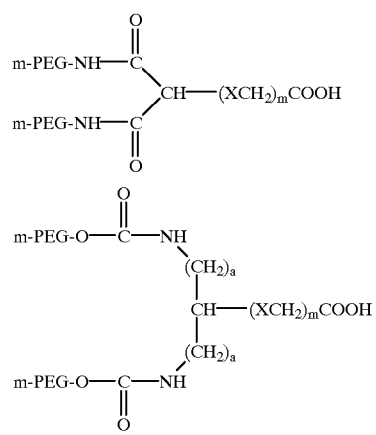

-continued

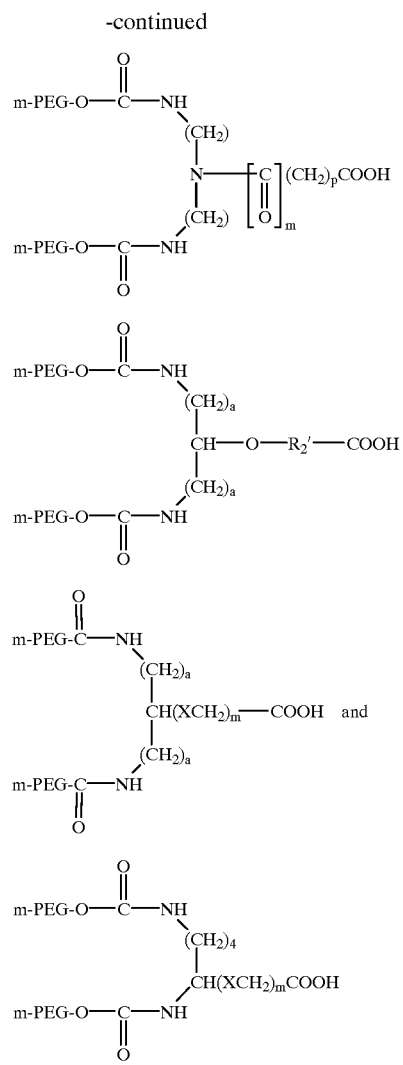

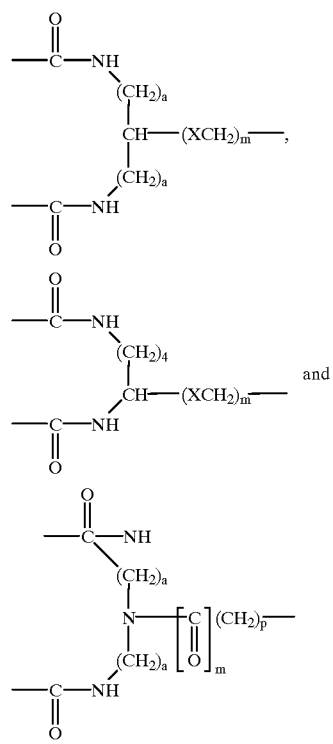

where (a), (m), (p) and X are as set forth above.

Some particularly preferred compounds within this aspect of the invention include:

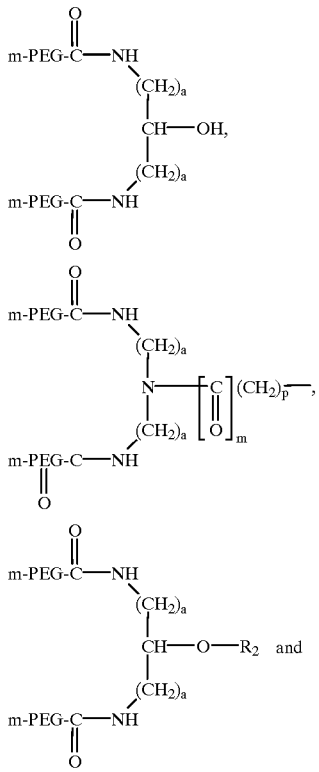

wherein:

(a) is an integer of from about 1 to about 5;

(m) is 0 or 1;

X is O, NQ, S, SO or $SO_2$; where Q is H, $C_{1-8}$ alkyl, $C_{1-8}$ branched alkyl, $C_{1-8}$ substituted alkyl, aryl or aralkyl;

(p) is 0 or an integer from about 1 to about 6; and $R_2'$ represents the corresponding spacer moiety $R_2$, described below, after undergoing the substitution reaction which results in the addition of the terminal carboxylic acid group.

It will, of course, be readily apparent to those of ordinary skill that the mPEG shown above for illustrative purposes can be replaced by any polyalklylene oxide or other substantially non-antigenic polymer described herein.

Another preferred embodiment of the invention includes branched polymers of the same formula set forth above, i.e. (I) and (Ia): $(R)_n L-A$, except that (L) is selected form the group consisting of

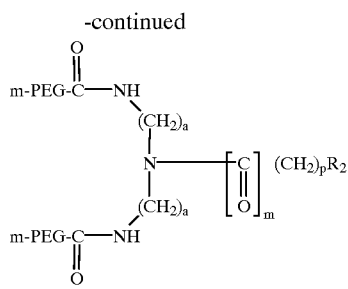

wherein:
(a) is an integer of from about 1 to about 5;
(m) is 0 or 1;
(p) is a positive integer, preferably from about 1 to about 6; and
$R_2$ is a spacer moiety selected form the group consisting of: polymers, —CO—NH—$(CH_2$—$)_d X_2$, —CO—NH—$(CH_2$—$CH_2$—O—$)_d X_2$,

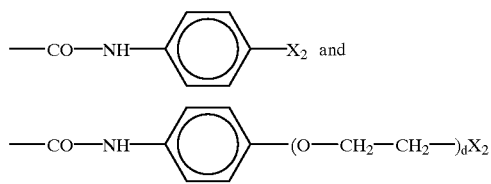

where (d) is an integer between about 1 and about 18 inclusive and ($X_2$) is H, OH, $NH_2$ or COOH, 2. Synthesis of Branched Polymers The branched polymers (generally, U-PAO's or U-PEG's) are formed using conventional reaction techniques. For each polymer chain (R) attached, the linking compound (L) has a number of nucleophilic functional groups which correspond to (n), (i.e. 2 or 3). In one aspect, a succinimidyl carbonate active ester of the branched polymer is prepared by contacting a branched polymer subunit $(R)_n L$, prepared as described above, with p-nitrophenyl chloroformate and thereafter with N-hydroxysuccinimide to form a succinimidyl carbonate. Alternatively, the hydroxy moiety can be reacted with bis-succinimidyl carbonate directly. The polymer subunit $(R)_n L$ will include hydroxyl, amino, carboxyl and thiol groups, and the like, as well as amino or methylene hydrogens so that it can be attached to (A).

The branched polymers can also be formed by reacting aliphatic linking compounds substituted with nucleophilic functional groups such as di- or tri-amino, mercapto alcohols or alkyl triols with an activated or functionalized polymer chain such as SC-PEG, PEG-NCO, PEG-NCS, SS-PEG, PEG-acids and acid derivatives. Such methods are preferred because functionalized polymer chains and suitable aliphatic linking groups are either commercially available or readily synthesized.

Other aspects of synthesis include reacting a polymer functionalized with a nucleophilic moiety such as PEG-alcohol, PEG-amine or PEG-mercaptan with bifunctional molecules such as malonic acid derivatives or glyoxalic acid derivatives.

For example, two moles of methoxy-poly(ethylene glycol) amine can be reacted with a substituted or unsubstituted malonyl chloride to form a compound of Formula (II):

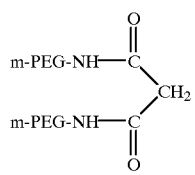

Reaction with strong base converts the methylene linker into an anion that can be further functionalized. For example, the anion can be reacted with diethyloxalate to yield the corresponding ketoester.

Likewise, two moles of methoxy-poly(ethylene glycol) succinimidyl carbonate may be reacted with a 1,3 diamino 2-propanol to form a compound of Formula (III):

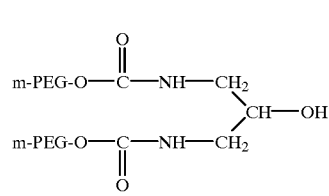

Similarly, two moles of mPEG-N-acyl-thiazolidine (hereinafter mPEG-FLAN) which can be prepared according to U.S. Pat. No. 5,349,001, the contents of which are incorporated herein by reference, can be reacted with a triamine such as diethylenetriamine to form a compound having the structure of Formula (IV):

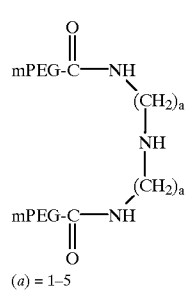

Branched polymers (III) and (IV) can then be activated. One manner of activation of (m) includes first functionalizing with compounds capable of activating the hydroxyl group such as p-nitrophenyl chloroformate to form a reactive p-nitrophenyl carbonate. The resulting p-nitrophenyl carbonate polymer can be directly reacted with a biologically active nucleophile.

The p-nitrophenyl carbonate polymer can also serve as an intermediate. It can be reacted with a large excess of N-hydroxysuccinimide to form a succinimidyl carbonate-activated branched polymer. Other routes to succinimidyl carbonates are available and contemplated for use herein. Alternatively, a p-nitrophenyl carbonate polymer intermediate can be reacted with anhydrous hydrazine to form a carbazate branched polymer.

Branched polymer (III) can also be activated by reacting it with an alkyl haloacetate in the presence of a base to form an intermediate alkyl ester of the corresponding polymeric carboxylic acid and thereafter reacting the intermediate alkyl ester with an acid such as trifluoroacetic acid to form the corresponding polymeric compound containing a terminal carboxylic acid. Preferably, tertiary allyl haloacetates are used. In particular, the carboxylic acid derivative is formed by:

i) contacting a branched polymer of the structure: $(R)_nL$-A, wherein (R),(n), (L) and (A) are as defined herein, with an alkyl haloacetate in the presence of a base to form an alkyl ester of a branched non-antigenic polymer; and ii) reacting the alkyl ester with an acid to form the branched polymer containing a reactive carboxylic acid thereon.

In carrying out the reaction, the molar ratio of the alkyl haloacetate to the branched polymer, i.e. polyalkylene oxide, is greater than 1:1. The reacting step ii) is carried out at a temperature of from about 0° to about 50° C. and preferably at a temperature of from about 20 to about 30° C. Optionally, the reacting step ii) can be carried out in the presence of water. Preferably, tertiary alkyl haloacetates of the formula:

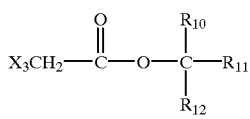

wherein:

$X_3$ is chlorine, bromine or iodine; and $R_{10-12}$ are independently selected from the group consisting of $C_{1-8}$ alkyls, $C_{1-8}$ substituted alkyls or $C_{1-8}$ branched alkyls and aryls are used.

Preferred tertiary alkyl haloacetates include tertiary butyl haloacetates such as t-butyl bromoacetate or t-butyl chloroacetate. Suitable bases include potassium t-butoxide or butyl lithium, sodium amide and sodium hydride. Suitable acids include trifluoroacetic acid or sulfuric, phosphoric and hydrochloric acids.

Branched polymer (IV) can be activated by reacting it with a hydroxy acid such as lactic acid or glycolic acid to form the hydroxy amide. Thereafter, the hydroxy amide is functionalized in the same manner discussed above for (III).

In another embodiment, two moles of methoxy-poly (ethylene glycol) acid or MPEG-FLAN can be reacted with 1,3-diamino-2-hydroxypropane to form a compound of formula (IIIa):

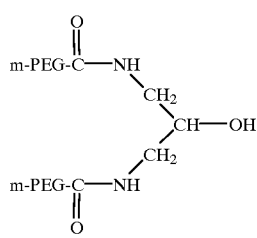

(IIIa)

Similarly, two moles of mPEG acid or, preferably, mPEG-FLAN can be reacted with a triamine such as diethylenetriamine to form a compound having the structure of Formula (IVa):

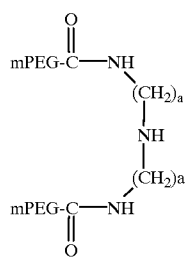

(IVa)

(a) in this case is 2.

Branched polymer (IIIa) and (IVa) can then be activated in the same way as described above with regard to compounds (III) and (IV).

In the case where m is zero (i.e. the carbonyl group is absent) synthesis of the branched polymer can be formed with a triamine (i.e. diethylenetriamine) being reacted with two equivalents of an acylating agent such as succinimidyl carbonate-activated PEG (SC-PEG), so that the terminal amino groups are functionalized with the PEG. This intermediate which contains a secondary amine is then alkylated with ethyl bromoacetate or t-butyl bromoacetate to yield the branched polymer.

In the case where m is one (i.e. a carbonyl group is present) synthesis of the branched polymer can be formed in a similar fashion. The terminal amines are functionalized with an activated PEG such as SC-PEG. Then, the residual secondary amine is reacted with another acylating agent such as succinic anhydride under more forceful conditions so that the less reactive tertiary amine is acylated.

As will be readily appreciated, numerous variations and combinations of the reaction between the functionalized polymer chains and aliphatic linking compound can be utilized to form the compounds of the present invention. The foregoing reactions were disclosed to illustrate the present invention.

Branched polymers corresponding to Formulas (II), (III), (IIIa), (IV), (IVa) and the like, can also be extended with a spacer moiety, designated herein as $R_2$, between the aliphatic linking moiety and the group capable of undergoing nucleophilic substitution. For example, the polymer of Formula (III) with a spacer moiety is represented by Formula (V):

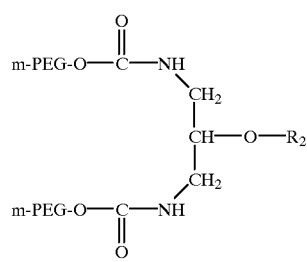

(V)

Spacer moieties represented by ($R_2$) include but are not limited to:

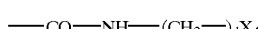
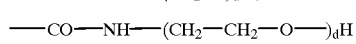

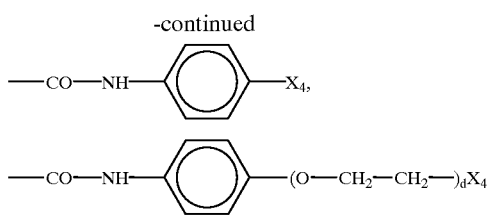

and the like, where (d) is an integer between 1 and 18 inclusive and ($X_4$) is OH, $NH_2$ or COOH. Depending upon the circumstances, an —H of an —OH group is attached to the end of the spacer moiety to form the terminal hydroxyl group. Thus, the spacer group is said to be proximal to L.

Synthesis of compounds corresponding to (V) include reacting the p-nitrophenyl carbonate or N-succinimidyl carbonate active esters of Formula (III) compounds with reagents such as $H_2N$—$(CH_2$—$)_d OH$,
$H_2N$—$(CH_2$—$CH_2$—$O$—$)_d H$,
aminophenols, or

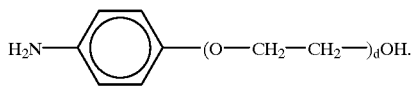

The compounds of Formulas (IIIa) and (IVa) can also be converted into the corresponding $R_2$ spacer-containing compounds in the same manner as that set forth above.

The attachment of spacer moieties to a branched polymer is described with reference to the polymer of Formula (II) for purposes of illustration, not limitation. Similar products would be obtained with any of the branched polymers disclosed by the present invention. For example, spacer moieties ($R_2$) can be joined to linker moieties (L) substituted with groups other than hydroxyl groups. When the hydroxyl group is replaced by an amino group, or when the carbon substituted with hydroxyl groups is replaced by a secondary amine, (L) can be reacted with suitable reagents such as substituted isocyanates or isothiocyanates and the like. Like the aliphatic linking moieties described above, the terminal groups of the spacer moieties can be similarly functionalized to react with nucleophiles, i.e. attachment of a suitable (A) moiety, i.e. COOH or other "activated terminal group".

After synthesis, the activated branched polymers can be purified by conventional methods and reacted with biologically active materials containing nucleophiles capable of bonding with the polymer while maintaining at least some of the activity associated with the material in unmodified form.

3. Biologically Active Materials Suitable for Conjugation

The nucleophiles conjugated with the branched polymers are described as "biologically active". The term, however, is not limited to physiological or pharmacological activities. For example, some nucleophile conjugates such as those containing enzymes, are able to catalyze reactions in organic solvents. Likewise, some inventive polymer conjugates containing proteins such as concanavalin A, immunoglobulin and the like are also useful as laboratory diagnostics. A key feature of all of the conjugates is that at least some portion of the activity associated with the unmodified bio-active material is maintained.

The conjugates are biologically active and have numerous therapeutic applications. Mammals in need of treatment which includes a biologically active material can be treated by administering an effective amount of a polymer conjugate containing the desired bioactive material. For example, mammals in need of enzyme replacement therapy or blood factors can be given branched polymer conjugates containing the desired material.

Biologically active nucleophiles of interest of the present invention include, but are not limited to, proteins, peptides, polypeptides, enzymes, organic molecules of natural and synthetic origin such as medicinal chemicals and the like.

Enzymes of interest include carbohydrate-specific enzymes, proteolytic enzymes, oxidoreductases, transferases, hydrolases, lyases, isomerases and ligases. Without being limited to particular enzymes, examples of enzymes of interest include asparaginase, arginase, arginine deaminase, adenosine deaminase, superoxide dismutase, endotoxinases, catalases, chymotrypsin, lipases, uricases, adenosine diphosphatase, tyrosinases and bilirubin oxidase. Carbohydrate-specific enzymes of interest include glucose oxidases, glucodases, galactosidases, glucocerebrosidases, glucouronidases, etc.

Proteins, polypeptides and peptides of interest include, but are not limited to, hemoglobin, both naturally occurring and recombinant mutant strains, serum proteins such as blood factors including Factors VII, VIII, and IX; immunoglobulins, cytokines such as interleukins, α-, β- and γ-interferons, colony stimulating factors including granulocyte colony stimulating factors, platelet derived growth factors and phospholipase-activating protein (PLAP). Other proteins of general biological or therapeutic interest include insulin, plant proteins such as lectins and ricins, tumor necrosis factors and related alleles, growth factors such as tissue growth factors, such as TGFα's or TGFβ's and epidermal growth factors, hormones, somatomedins, erythropoietin, pigmentary hormones, hypothalamic releasing factors, antidiuretic hormones, prolactin, chorionic gonadotropin, follicle-stimulating hormone, thyroid-stimulating hormone, tissue plasminogen activator, and the like. Immunoglobulins of interest include IgG, IgE, IgM, IgA, IgD and fragments thereof.

Some proteins such as the interleukins, interferons and colony stimulating factors also exist in non-glycosylated form, usually as a result of using recombinant techniques. The non-glycosylated versions are also among the biologically active nucleophiles of the present invention.

The biologically active nucleophiles of the present invention also include any portion of a polypeptide demonstrating in vivo bioactivity. This includes amino acid sequences, antisense moieties and the like, antibody fragments, single chain binding antigens, see, for example U.S. Pat. No. 4,946,778, disclosure of which is incorporated herein by reference, binding molecules including fusions of antibodies or fragments, polyclonal antibodies, monoclonal antibodies, catalytic antibodies, nucleotides and oligonucleotides.

The proteins or portions thereof can be prepared or isolated by using techniques known to those of ordinary skill in the art such as tissue culture, extraction from animal sources, or by recombinant DNA methodologies. Transgenic sources of the proteins, polypeptides, amino acid sequences and the like are also contemplated. Such materials are obtained form transgenic animals, i.e., mice, pigs, cows, etc., wherein the proteins expressed in milk blood or tissues. Transgenic insects and baculovirus expression systems are also contemplated as sources. Moreover, mutant versions of proteins, such as mutant TNF's and/or mutant interferons are also within the scope of the invention.

Other proteins of interest are allergen proteins such as ragweed, Antigen E, honeybee venom, mite allergen, and the like.

Useful biologically active nucleophiles are not limited to proteins and peptides. Essentially any biologically-active compound is included within the scope of the present invention. The present invention is particularly well-suited for compounds which have few or even a single nucleophilic attachment site for polymer conjugation such as medicinal chemicals whether isolated from nature or synthesized. Chemotherapeutic molecules such as pharmaceutical chemicals i.e. anti-tumor agents such as paclitaxel, taxotere, related taxoteres, taxoid molecules, camptothecin, podophyllotoxin, anthracyclines, methotrexates, etc. cardiovascular agents, anti-neoplastics, anti-infectives, anti-anxiety agents, gastrointestinal agents, central nervous system-activating agents, analgesics, fertility or contraceptive agents, anti-inflammatory agents, steroidal agents, anti-urecemic agents, cardiovascular agents, vasodilating agents, vasoconstricting agents and the like.

The foregoing is illustrative of the biologically active nucleophiles which are suitable for conjugation with the polymers of the invention. It is to be understood that those biologically active materials not specifically mentioned but having suitable nucleophilic groups are also intended and are within the scope of the present invention.

4. Synthesis of Biologically Active Conjugates

One or more of the activated branched polymers can be attached to a biologically active nucleophile by standard chemical reactions. The conjugate is represented by the formula:

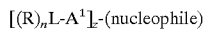

wherein (R) is a water-soluble substantially non-antigenic polymer; n=2 (L) is an aliphatic linking moiety; ($A^1$) represents a linkage between (L) and the nucleophile and (z) is an integer <1 representing the number of polymers conjugated to the biologically active nucleophile. The upper limit for (z) will be determined by the number of available nucleophilic attachment sites and the degree of polymer attachment sought by the artisan. The degree of conjugation can be modified by varying the reaction stoichiometry using well-known techniques. More than one polymer conjugated to the nucleophile can be obtained by reacting a stoichiometric excess of the activated polymer with the nucleophile.

The biologically active nucleophiles can be reacted with the activated branched polymers in an aqueous reaction medium which can be buffered, depending upon the pH requirements of the nucleophile. The optimum pH for the reaction is generally between about 6.5 and about 8.0 and preferably about 7.4 for proteinaceous/polypeptide materials. Organic/chemotherapeutic moieties can be reacted in non-aqueous systems. The optimum reaction conditions for the nucleophile's stability, reaction efficiency, etc. is within level of ordinary skill in the art. The preferred temperature range is between 4° C. and 37° C. The temperature of the reaction medium cannot exceed the temperature at which the nucleophile may denature or decompose. It is preferred that the nucleophile be reacted with an excess of the activated branched polymer. Following the reaction, the conjugate is recovered and purified such as by diafiltration, column chromatography, combinations thereof, or the like.

It can be readily appreciated that the activated branched non-antigenic polymers of the present invention are a new and useful tool in the conjugation of biologically active materials, especially when they lack a sufficient number of suitable polymer attachment sites.

EXAMPLES

The following non-limiting examples illustrate certain aspects of the invention. All parts and percentages are by weight unless otherwise noted and all temperatures are in degrees Celsius.

Materials

Methoxypoly(ethylene glycol) (m-PEG) (mw=5,000) was obtained from Union Carbide. The solvents were obtained from Aldrich Chemical of Milwaukee, Wis. The methoxypoly(ethylene glycol)-N-succinimidyl carbonate (SC-PEG) was prepared as described in U.S. Pat. No. 5,122,614, using m-PEG having a molecular weight of about 5,000. The m-PEG-FLAN was prepared as described in U.S. Pat. No. 5,349,001. Each of the products prepared in Examples 1–9 were confirmed structurally by carbon—13 NMR.

Example 1

U-PEG-OH

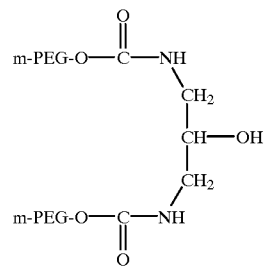

This branched polymer was prepared by adding 100 mg (1.1 mmol) of 1,3-diamino-2-propanol to a solution of 10.0 g (2 mmol) of SC-PEG in 50 mL of methylene chloride. The mixture was stirred for 18 hours at room temperature then filtered. Excess solvent was removed by distillation in vacuo. The residue was recrystallized from 2-propanol to yield 7.1 g of product (70% yield).

Example 2

U-PNP-PEG

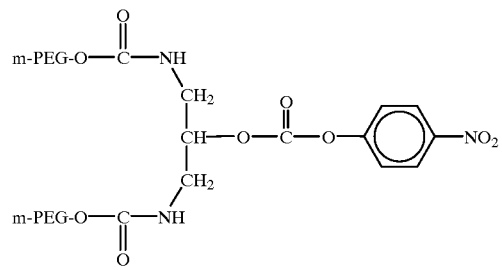

The compound of Example 1 was activated with p-nitrophenyl chloroformate. First, 5.0 g (0.5 mmol) of U-PEG was azeotropically dried by refluxing in 75 mL of toluene for 2 hours, resulting in the removal of 25 mL of solvent/water. The reaction mixture was cooled to 30° C., followed by the addition of 120 mg (0.6 mmol) of p-nitrophenyl chloroformate and 50 mg (0.6 mmol) of pyridine. The resulting mixture was stirred for two hours at 45° C., followed by stirring overnight at room temperature.

The reaction mixture was then filtered through CELITE™, followed by removal of the solvent from the filtrate by distillation in vacuo. The residue was recrystallized from 2-propanol to yield 4.2 g (81% yield) of the product.

Example 3
US-PEG

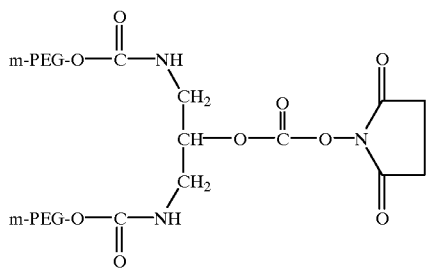

In this example, the U-PNP PEG of Example 2 was reacted with N-hydroxysuccinimide to form the succinimidyl carbonate ester of U-PEG. A solution containing 5.0 g (0.5 mmol) of the U-PNP PEG, 0.6 g (5 mmol) of N-hydroxysuccinimide and 0.13 g (1 mmol) of diisopropylethylamine in 40 ml of methylene chloride was refluxed for 18 hours. The solvent was then removed by distillation in vacuo, and the residue was recrystallized from 2-propanol to yield 4.2 g of the succinimidyl carbonate ester (82% yield).

Example 4
NU-PNP-PEG

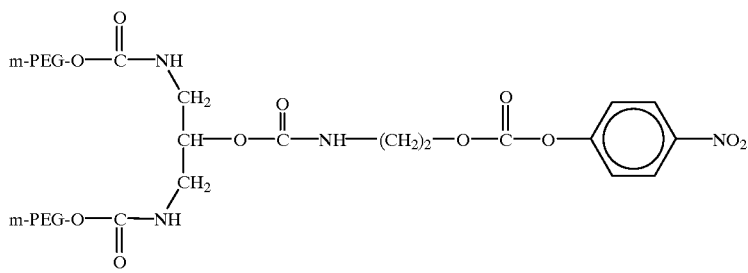

This branched polymer above was prepared by reacting U-PNP PEG (Ex. 2) with ethanolamine followed by p-nitrophenyl chloroformate.

A solution containing 5.0 g (0.5 mmol) of U-PNP PEG in 40 mL of methylene chloride was combined with 60 mg (1 mmol) of ethanolamine and stirred overnight at room temperature. Thereafter, the solvent was removed by distillation in vacuo.

The residue was recrystallized from 2-propanol to yield 4.3 g of the intermediate compound 4a (84% yield) shown below:

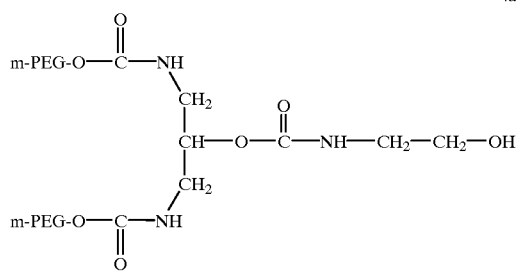

The NU-PEG-OH was prepared by reacting the above intermediate with p-nitrophenyl chloroformate. The intermediate was azeotropically dried by refluxing, 2.0 g (0.2 mmol) in 40 mL toluene for two hours, with the removal of 25 mL of solvent/water. The reaction mixture was cooled, followed by the addition of 0.3 mmol p-nitrophenyl chloroformate and 0.3 mmol pyridine, according to the procedure of Example 2. The resulting mixture was stirred for two hours at 45° C., followed by stirring overnight at room temperature.

The NU-PEG-OH was also recovered by the procedure in Example 2 to yield 1.5 g (71% yield).

Example 5
XU-PEG-OH

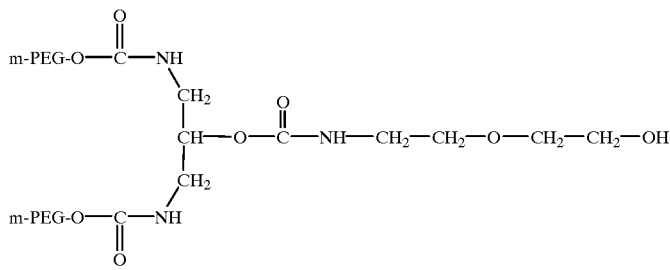

This branched polymer was prepared by reacting the U-PNP PEG of Example 2 with 2-(2-aminoethoxy) ethanol according to the procedure described in Example 4, (i.e., the amino alcohol was reacted with the p-nitrophenyl carbonate). The recrystallized product yield was 86%.

Example 6
XU-PNP-PEG

The compound of Example 5 was functionalized with p-nitrophenyl carbonate as in Examples 2 and 4. The recrystallized product yield was 83%.

Example 7
XUS-PEG

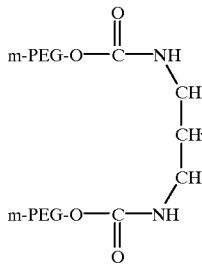

In this example, the succinimidyl carbonate derivative of compound prepared in Example 5 was prepared according to the process described in Example 3, by reacting N-hydroxysuccinimide with the p-nitrophenyl carbonate derivative of Example 6. The recovered product yield was 84%.

Example 8
U-LYS-PEG

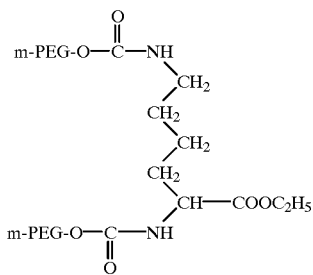

The branched polymer depicted above was prepared by reacting m-PNP PEG with lysine ethyl ester. In particular, a mixture of 5.0 g (1.0 mmol) of the polymer, 150 mg (0.6 mmol) of lysine dihydrochloride and 140 mg (1.8 mmol) of pyridine was refluxed for 18 hours. The solvent was removed by distillation in vacuo. The residue was recrystallized from 2-propanol to yield 4.5 g (88% yield) of product.

Example 9
Synthesis of m-PNP-PEG

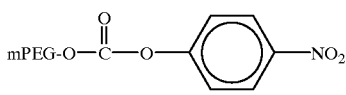

A solution of 50 g (0.01 moles) of m-PEG-OH (MW= 5000) in 500 ml of toluene was azeotroped for 2 hrs, while removing 100 ml of toluene/water. The reaction mixture was cooled to 30° C., followed by addition of 2.6 g (0.013 moles) of p-nitrophenyl chloroformate and 1.0 mil (0.013 moles) of pyridine. The resulting mixture was stirred for two hours at 45° C., followed by stirring overnight at room temperature. The reaction mixture was then filtered through CELITE™, followed by removal of the solvent by distillation in vacuo. The residue was recrystallized from 2-propanol to yield 48.2 g (93% yield) of the product.

Examples 10 and 11

Conjugates of erythropoietin (EPO) with US-PEG (Example 3) were prepared by dialyzing two 3.0 mg EPO 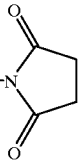 samples (human recombinant Chinese Hamster Ovary (CHO) cell culture) into 0.1 M phosphate buffer pH 7.0 solutions using a Centricon-10 (Amicon Corporation, Beverly, Mass.). The first EPO solution was combined with 1–954 mg (2-fold molar excess) of the US-PEG while the second EPO solution was combined with 3.908 mg (4-fold molar excess) of the US-PEG. The reaction mixtures were stirred for one hour at room temperature (about 22–25° C.). The excess polymer was removed by centrifugation and the reaction mixtures were dialyzed into 10 mM phosphate buffer, pH 8.0. Unreacted EPO was removed on an ion-exchange column (2-HD column, Sepracor).

SDS-PAGE analysis confirmed that for both reaction mixtures, about two to three of the branched polymers were covalently bound to each protein molecule. The EPO activity of the conjugates was measured by colorometric assay with DA 1-K cells, a murine lymphoblastic cell line dependent on IL-3, GM-CSF and EPO for growth. The cells are grown in IMDM containing 5% FCS and incubated at 37° C. in 5% $CO_2$ in air. The assay time is 72 hours and cell growth is monitored by MTT dye uptake. In the assay, both conjugate samples retained 40–50% of the activity of the unconjugated EPO.

Examples 12 and 13

Tumor Necrosis Factor (TNF) was conjugated with the XUS-PEG of Example 7. As a comparison, the TNF was also conjugated with the linear SC PEG, methoxypoly (ethylene glycol) succinimidyl carbonate of U.S. Pat. No. 5,122,614. Both conjugates were prepared by reacting a 500 micrograms of TNF, 2.0 mg/mL, with a 25-fold molar excess of the polymer. Each reaction was carried out for 140 minutes on ice.

The $ED_{50}$ for the branched conjugate was 0.29 ng/ml for the concentration-response curve generated by dilutions of 0.1 micrograms/mL and 0.625 ng/mL for the concentration-response curve generated by dilutions of 0.01 micrograms/ mL. The $ED_{50}$ for unmodified TNF of 0.01–0.02 ng/mL. The $ED_{50}$ for the linear succinimidyl carbonate conjugates, ranged between 8 and 19 ng/mL.

In vitro tumoricidal and toxicity data indicated that the branched conjugate appears to be more cytotoxic than the non-branched conjugate.

Example 14

U-PEG carboxylic acid t-butyl ester

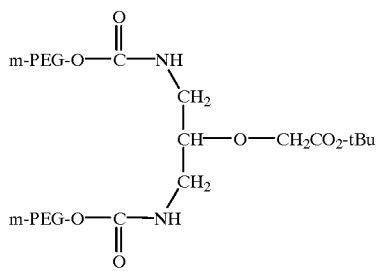

A solution of 1.0 g. (0.099 mmol) of U-PEG-OH in 30 mL of toluene was azeotroped with the removal of 10 mL of distillate. The reaction mixture was cooled to 30° C., followed by the addition of 50 μL (0.34 mmol) of t-butyl bromoacetate and 0.1 mL (1.0 mmol) of 1.0 M potassium t-butoxide in t-butanol. The resulting mixture was stirred at 40° C. overnight. The reaction mixture was filtered through a Celite pad followed by removal of the solvent by distillation in vacuo. The residue was recrystallized from 2-propanol to yield 0.98 g (97% recovery). The product contained 60% of the desired t-butyl ester as determined from $^{13}$C NMR.

$^{13}$C NMR: $(CH_3)_3C$—, 27.54 ppm; —$CH_2NH$—, 45.31 ppm; —O—$CH_3$, 58.40 ppm; $(CH_3)_3C$—, 80.21 ppm; —OC(=O) NH—, 157.20 ppm; —C(=O)O—, 166.89 ppm.

Example 15

U-PEG carboxylic acid

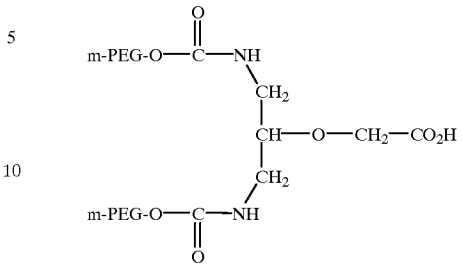

A solution of 0.5 g (0.049 mmol) of U-PEG carboxylic acid t-butyl ester and 2.5 mL of trifluoracetic acid in 5 mL of methylene chloride is stirred at toom temperature for 3 hours. The solvent is then removed by distillation in vacuo, followed by recrystallization of the residue from chilled methylene chloride/ethyl ether (20% v/v methylene chloride in ether, total ca. 20 mL) to yield 0.42 g (85% yield) of product.

$^{13}$C NMR: —$CH_2NH$—, 43.31 ppm; —$OCH_3$, 58.04 ppm; —OC(=O) NH—, 156.20 ppm; —C(=O)O—, 169.89 ppm.

Example 16

NU-PEG-carboxylic acid

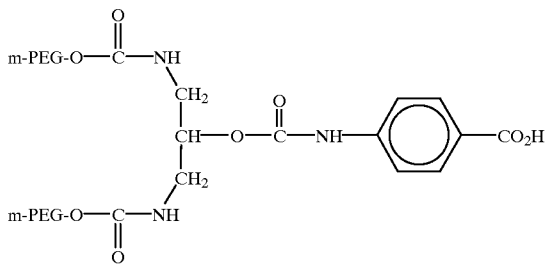

This branched polymer above was prepared by reacting US-PEG (Ex. 3) with methylparaaminobenzoate followed by selective hydrolysis to provide the branched polymer containing the terminal carboxylic acid.

Example 17

XU-PEG-carboxylic acid:

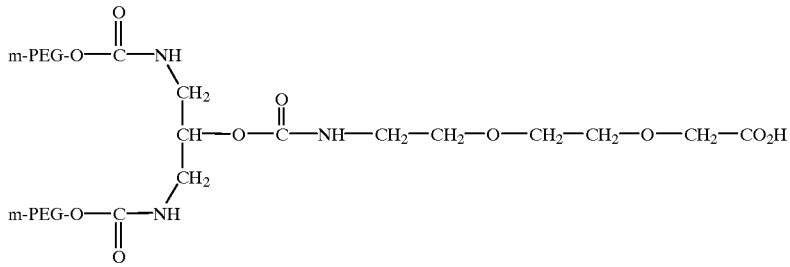

In this example, the carboxylic acid derivative of compound Example 5 (XU-PEG-OH) was prepared according to the processes described in the Examples 14 and 15 wherein the terminal carboxylic acid derivative was formed.

Example 18

Amine-Based U-PEG-OH

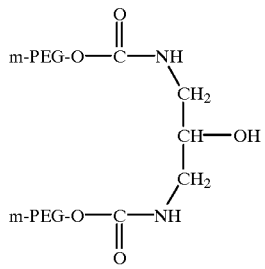

To a solution of 10.0 g (2 mmoles) of m-PEG-Flan prepared in accordance with previously mentioned U.S. Pat. No. 5,349,001, in 50 ml of methylene chloride is added 100 mg (1.1 mmoles) of 1,3-diamino-2-propanol. This mixture is then stirred for 18 hours at room temperature, followed by filtration and removal of the solvent by distillation in vacuo. The resulting residue is recrystallized from 2-propanol to yield 7.1 g of product.

$^{13}$C NMR assignments: $CH_2NH$, 43.2 ppm; $OCH_3$, 58.1 ppm; CHOH, 63.0 ppm; —C—O, 171.2 ppm.

Example 19

Amine-Based U-PEG-COOH

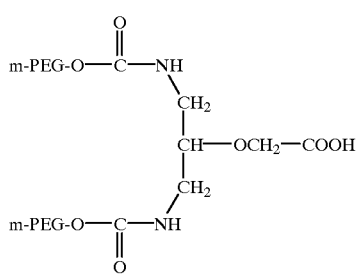

The corresponding carboxylic acid derivative of the compound of Example 18 was formed using the procedures set forth in Examples 14 and 15.

Example 20

NU-PEG AMINE-OH

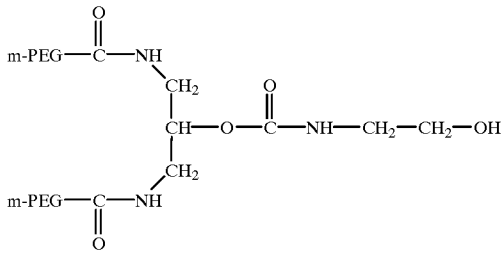

This branched polymer was formed by repeating the steps of Example 4 to yield compound 4a using the compound of Example 18 as the starting compound.

Example 21

XU-PEG AMINE-OH

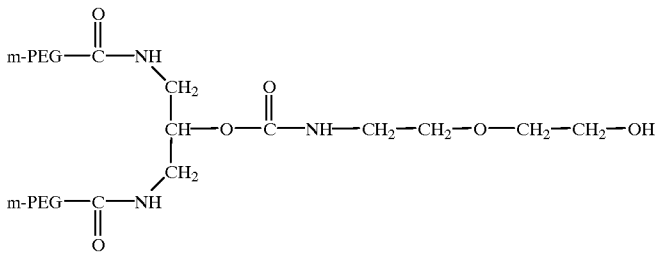

This branched polymer was formed by repeating Example 5 with the compound of Example 18.

Example 22

20-S Camptothecin-U-PEG 5,000

A mixture of 4.0 g (0.4 mmoles) of U-PEG carboxylic acid prepared in Example 15, 0.28 g (0.8 mmoles) of camptothecin, 0.10 g (0.8 mmoles) of diisopropylcarbodiimide and 0.10 g (0.8 mmoles) of 4-dimethylaminopyridine is added to 50 ml of anhydrous dichloromethane at 0° C. This mixture is allowed to warm up to room temperature, and stirring is continued for 18 hours, followed by removal of the solvent by distillation in vacuo. The residue is recrystallized from 2-propanol to yield 3.4 g of the title product.

Example 23

2'-Paclitaxel,U-PEG 5,000

A mixture of 4.0 g (0.4 mmoles) of NU-PEG carboxylic acid prepared in Example 16, 0.68 g (0.08 mmoles) of paclitaxel, 0.10 g (0.8 mmoles) of diisopropylcarbodiimide and 0.10 g (0.8 mmoles) of 4-dimethylaminopyridine is added to 50 ml of anhydrous dichloromethane at 0° C. This mixture is allowed to warm up to room temperature, and stirring is continued for 18 hours, followed by removal of the solvent by distillation in vacuo. The residue is recrystallized from 2-propanol to yield 3.4 g of the titled product.

Example 24

2'-PACLITAXEL-U-PEG 5.000

A mixture of 4.0 g (0.4 mmoles) of the compound of Example 19 U-PEG, 0.68 g (0.8 mmoles) of paclitaxel, 0.10 g (0.8 mmoles) of diisopropylcarbodiimide and 0.10 g (0.8 mmoles) of 4-dimethylaminopyridine is added to 50 ml of anhydrous dichloromethane at 0° C. This mixture is allowed to warm up to room temperature, and stirring is continued for 18 hours, followed by removal of the solvent by distillation. The residue is recrystallized from 2-propanol to yield 3.4 g of the titled product.

What is claimed is:

1. A substantially non-antigenic polymer of the formula:

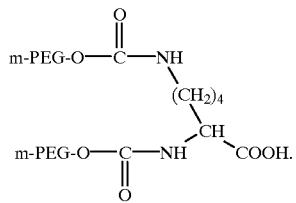

2. A substantially non-antigenic polymer of the formula:

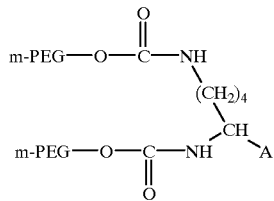

wherein (A) is a functional group capable of bonding with a biologically active nucleophile, or a spacer moiety capable of being functionalized to react with a biologically active nucleophile.

3. A substantially non-antigenic polymer of the formula:

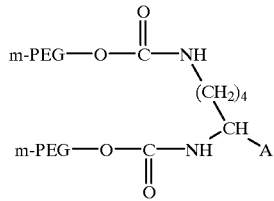

wherein (A) is a functional group of a biologically active material capable of reacting with an amino group.

4. A substantially non-antigenic polymer conjugate of the formula:

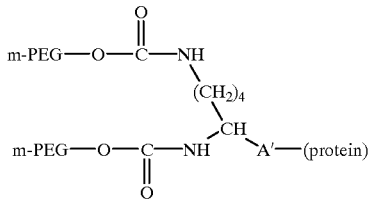

wherein (A') is a linkage moiety.

5. A branched substantially non-antigenic polymer of the formula:

$(R)_nL-A$ wherein:

(R) is a monomethyl polyethylene glycol;

(n) is 2;

(A) is a functional group capable bonding with a biologically active nucleophile, or a spacer moiety capable of being functionalized to react with a biologically active nucleophile (L) is: 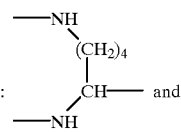 and wherein each (R) is linked to (L) by a urethane linkage.

6. A polymeric conjugate of the formula:

$[(R)_nL-A^1]_z$-(nucleophile)

wherein:

(R) is a monomethyl polyethylene glycol;

(n) is 2;

(L) is: 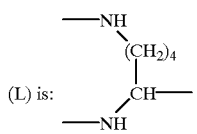

wherein each (R) is linked to (L) by a urethane linkage, (A') represents a linkage between (L) and the biologically active nucleophile;

(z) is an integer $\leq 1$; and (nucleophile) is a biologically active nucleophile.

7. The polymeric conjugate of claim 6, wherein the (nucleophile) is α-interferon and (z) is one.

8. A substantially non-antigenic polymer conjugate of the formula:

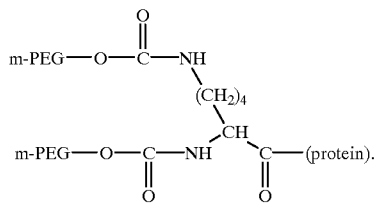

9. The conjugate of claim 8, wherein said protein is an interferon.

10. The polymer conjugate of claim 9, wherein said interferon is an α-interferon.

11. A substantially non-antigenic polymer conjugate of the formula:

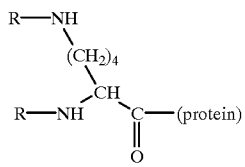

wherein each (R) is a water-soluble substantially non-antigenic polymer containing a $C_{1-4}$ terminal group, each (R) is linked to each NH via a urethane bond and the polymer portion thereof has a molecular weight of less than about 80,000 Daltons.

12. The conjugate of claim 11, wherein said protein is an interferon.

13. The polymer conjugate of claim 12, wherein said interferon is an α-interferon.

14. The conjugate of claim 11, wherein each (R) is a polyalkylene oxide.

15. The conjugate of claim 14, wherein said polyalkylene oxide is polyethylene glycol.

16. The conjugate of claim 15, wherein said polyalkylene oxide is monomethoxypolyethylene glycol.

17. The substantially non-antigenic polymer of claim 1, wherein the molecular weight of said polymer is less than about 80,000 Daltons.

18. The substantially non-antigenic polymer conjugate of claim 4, wherein the molecular weight of the polymer portion thereof is less than about 80,000 Daltons.

19. The substantially non-antigenic polymer conjugate of claim 8, wherein the molecular weight of the polymer portion thereof is less than about 80,000 Daltons.

20. The substantially non-antigenic polymer conjugate of claim 11, wherein the molecular weight of the polymer portion thereof is less than about 80,000 Daltons.

* * * * *

UNITED STATES PATENT AND TRADEMARK OFFICE
CERTIFICATE OF CORRECTION

PATENT NO. : 6,113,906
DATED : September 5, 2000
INVENTOR(S) : Greenwald, R.B., et al.

It is certified that error appears in the above-identified patent and that said Letters Patent is hereby corrected as shown below:

Column 5,
Line 5, delete "MPEG", insert -- mPEG --;

Column 10,
Line 49, delete "(m)", insert -- (III) --;

Column 11,
Line 48, delete "MPEG-FLAN", insert -- mPEG-FLAN --.

Claim 3,
Lines 3-4, after "group" delete "of a biologically active material";
Line 4, after "group" insert -- of a biologically active material --;

Claim 5,
Line 7, after "capable" insert -- of --;
Line 10, after "nucleophile" insert -- ; --;

Claim 6,
Line 10, change "$\leq 1$" to -- $\geq 1$ --.

Signed and Sealed this

Sixth Day of November, 2001

Attest:

*Nicholas P. Godici*

NICHOLAS P. GODICI
*Attesting Officer*    *Acting Director of the United States Patent and Trademark Office*

Adverse Decisions in Interference

Patent No. 6,113,906, Richard B. Greenwald, Anthony J. Martinez, WATER-SOLUBLE NON- ANTIGENIC POLYMER LINKABLE TO BIOLOGICALLY ACTIVE MATERIAL, Interference No. 105,414, final judgment adverse to the patentees rendered October 16, 2006, as to claims 7, 9, 10, 12, and 13.

*(Official Gazette April 17, 2007)*